United States Patent
Kubalak et al.

(10) Patent No.: US 9,855,144 B2
(45) Date of Patent: Jan. 2, 2018

(54) PENILE PROSTHETIC WITH AN INSERTION TOOL CONTAINED INSIDE AN INFLATABLE BLADDER

(71) Applicant: Coloplast A/S, Humlebaek (DK)

(72) Inventors: Thomas Kubalak, Wayzata, MN (US); Donald Wolf, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 84 days.

(21) Appl. No.: 14/873,207

(22) Filed: Oct. 2, 2015

(65) Prior Publication Data

US 2017/0065419 A1    Mar. 9, 2017

Related U.S. Application Data

(60) Provisional application No. 62/215,748, filed on Sep. 9, 2015.

(51) Int. Cl.
  *A61F 2/26*    (2006.01)

(52) U.S. Cl.
  CPC ..................... *A61F 2/26* (2013.01)

(58) Field of Classification Search
  CPC .......................................... A61F 2/26
  USPC .................................... 600/38–41
  See application file for complete search history.

(56) References Cited

U.S. PATENT DOCUMENTS

| | | |
|---|---|---|
| 1,410,296 A | 3/1922 | Osborne |
| 3,639,561 A * | 2/1972 | Gordon et al. ...... A61K 9/0034 |
| | | 424/431 |
| 3,722,104 A | 3/1973 | Enzetti |
| 4,201,202 A | 5/1980 | Finney et al. |
| 4,244,370 A | 1/1981 | Furlow et al. |
| 4,318,396 A * | 3/1982 | Finney ...................... A61F 2/26 |
| | | 600/40 |
| 4,335,714 A | 6/1982 | Edgerton et al. |
| 4,350,151 A | 9/1982 | Scott |
| 4,558,693 A | 12/1985 | Lash et al. |
| 4,590,927 A | 5/1986 | Porter et al. |
| 4,602,621 A | 7/1986 | Hakky |
| 4,628,912 A | 12/1986 | Fischell |
| 4,653,485 A | 3/1987 | Fishell |
| 4,904,183 A | 2/1990 | Hannan et al. |
| 4,988,357 A | 1/1991 | Koss |
| 5,010,882 A | 4/1991 | Polyak et al. |
| 5,056,223 A | 10/1991 | Buck et al. |

(Continued)

FOREIGN PATENT DOCUMENTS

| | | |
|---|---|---|
| CN | 2059828 U | 8/1990 |
| CN | 2093615 U | 1/1992 |

(Continued)

*Primary Examiner* — Samuel Gilbert
(74) *Attorney, Agent, or Firm* — Coloplast Corp., Coloplast A/S; Nick Baumann

(57) ABSTRACT

A penile prosthetic includes an insertion tool contained inside of an inflatable bladder of a penile implant. The penile implant is sized for insertion into a dilated corpora cavernosum of a penis. The penile implant has a proximal tip that is insertable into the crus penis, with the inflatable bladder connected to the proximal tip. The inflatable bladder has a first column strength and includes a distal tip that is insertable into the glans penis. The insertion tool provides the inflatable bladder with an effective column strength that is greater than the first column strength.

15 Claims, 10 Drawing Sheets

(56) References Cited

U.S. PATENT DOCUMENTS

| | | |
|---|---|---|
| 5,088,925 A | 2/1992 | Mason |
| 5,167,611 A | 12/1992 | Cowan |
| 5,281,230 A | 1/1994 | Heidmueller |
| 5,484,450 A | 1/1996 | Mohamed |
| 5,968,067 A | 10/1999 | Mooreville et al. |
| 6,679,832 B1 | 1/2004 | Sultan |
| 6,808,489 B2 | 10/2004 | George et al. |
| 7,066,878 B2 | 6/2006 | Eid |
| 7,169,103 B2 | 1/2007 | Ling et al. |
| 7,172,602 B2 | 2/2007 | George et al. |
| 7,390,296 B2 * | 6/2008 | Mische ............... A61F 2/26 600/40 |
| 8,231,521 B2 | 7/2012 | Morningstar et al. |
| 2002/0193659 A1 | 12/2002 | Yachia et al. |
| 2003/0220539 A1 | 11/2003 | George et al. |
| 2003/0220540 A1 | 11/2003 | Kuyava |
| 2004/0010244 A1 | 1/2004 | George et al. |
| 2004/0215056 A1 | 10/2004 | Ling et al. |
| 2004/0225182 A1 | 11/2004 | Eid |
| 2005/0014993 A1 | 1/2005 | Mische |
| 2007/0175487 A1 | 8/2007 | Eid |
| 2007/0283969 A1 | 12/2007 | Yamasaki et al. |
| 2009/0132044 A1 | 5/2009 | George et al. |
| 2009/0137867 A1 | 5/2009 | Goto |
| 2011/0144427 A1 | 6/2011 | Morningstar et al. |
| 2011/0144428 A1 | 6/2011 | Morningstar et al. |

FOREIGN PATENT DOCUMENTS

| | | |
|---|---|---|
| CN | 2127302 Y | 2/1993 |
| CN | 2168565 Y | 6/1994 |
| CN | 2464274 Y | 12/2001 |
| CN | 1328809 A | 1/2002 |
| CN | 1341406 A | 3/2002 |
| CN | 1859882 A | 11/2006 |
| CN | 1893894 A | 1/2007 |
| EP | 0682923 A1 | 11/1995 |
| GB | 2163354 A1 | 2/1986 |
| JP | 2009131310 A2 | 6/2009 |
| WO | 0167996 A2 | 9/2001 |
| WO | 03071970 A1 | 9/2003 |
| WO | 2004045421 A1 | 6/2004 |
| WO | 2008/008547 | 1/2008 |
| WO | 2010087768 A1 | 8/2010 |
| WO | 2012097818 A1 | 7/2012 |

* cited by examiner

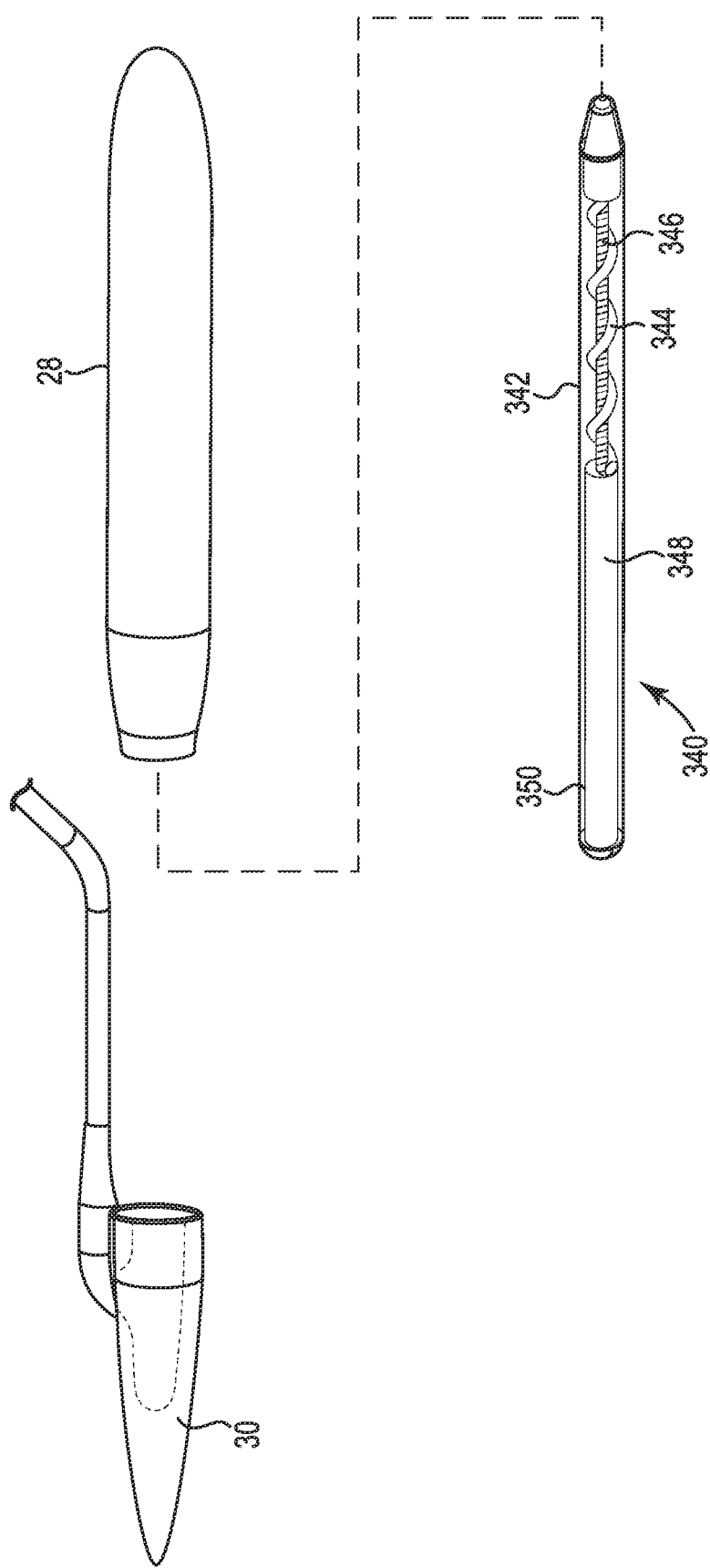

PENILE PROSTHETIC WITH AN INSERTION TOOL CONTAINED INSIDE AN INFLATABLE BLADDER

SUMMARY

One aspect provides a penile implant having a proximal tip that is insertable into a crus penis, an inflatable bladder having a distal tip that is insertable into a glans penis, with the inflatable bladder sealed to the proximal tip, and an insertion tool disposed in the inflatable bladder. The insertion tool remains in the inflatable bladder after implantation of the penile implant.

The insertion tool allows the surgeon to push the penile implant into the penis without the use of secondary tools, such as a Furlow device or a Keith needle.

The insertion tool provides the penile implant with sufficient rigidity to allow the penile implant to be inserted into a corporotomy and subsequently pushed in a distal direction into the glans penis. In the presence of liquid, for example when the surgeon inflates the inflatable bladder to confirm the function of the device, or within 8-24 hours after insertion, the insertion tool softens to become a pliable space occupier inside of the inflatable bladder, or dissolves into solution with the liquid.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 11 is an exploded side view of one embodiment of a penile implant including a malleable rod removed out of containment from inside of an inflatable bladder that is sealable to a proximal tip of the penile implant.

DETAILED DESCRIPTION

Figure 1:
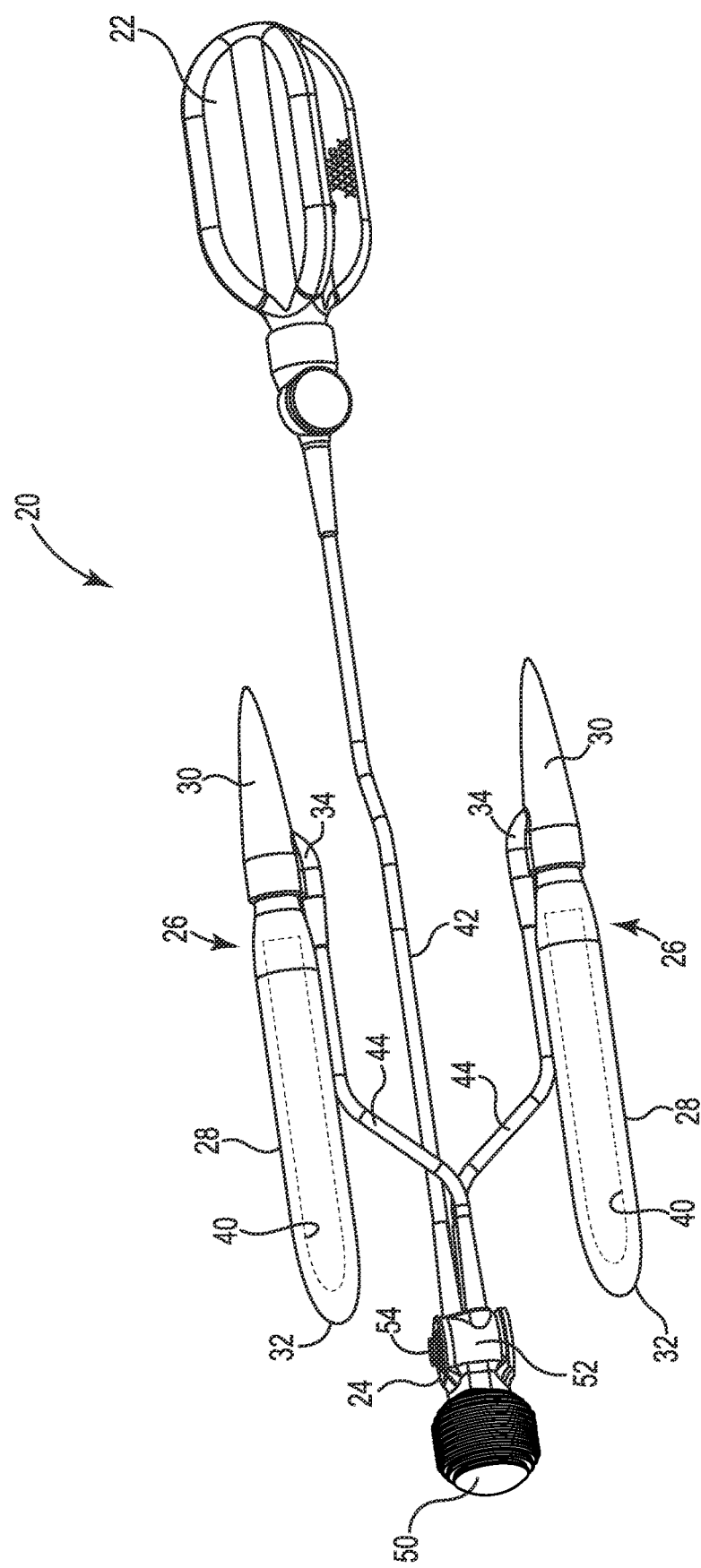
FIG. 1 is a perspective view of one embodiment of a penile prosthetic including a pump connected to two penile implants and a reservoir.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthetic has proven useful in treating erectile dysfunction in men. One acceptable implanted penile prosthetic includes two inflatable cylinders implanted in the penis, a pump implanted in the scrotum or other internal space of the body, and a liquid holding reservoir implanted in the abdomen or other internal space of the body, with the pump connected to the cylinders and the reservoir.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic.

Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is attached to the Furlow introducer. The Keith needle could possibly fall out of the Furlow introducer, so the surgical staff handles the tool with care. The surgeon inserts the Furlow introducer into the dilated corpora cavernosum. The surgeon steadies the Furlow introducer with one hand and pushes a plunger (or obturator) of the Furlow introducer with the other hand. Pushing the plunger pushes the needle from of the introducer, through tissue of the penis, and out the glans penis. The exposed portion of the needle is handled by the surgeon, removed from the suture, and discarded. The remaining suture is subsequently employed to tow the cylinder into place within the dilated corpora cavernosum.

The above-described procedure has proven effective when implanting penile prostheses. However, surgeons would appreciate having fewer parts to handle during the procedure. In addition, surgeons and those handling the Keith needle would possibly welcome a tool for implanting a penile prosthetic that reduces or eliminates their exposure to the Keith needle.

This disclosure describes several embodiments that address the problem of the Keith needle falling out of a Furlow tool during the procedure and the surgeon handling a variety of components including a needle, a suture, and a Furlow tool by providing a solution where an insertion tool is enclosed inside of the penile implant to provide an effective column strength allowing insertion of the implant into the penis without external tools, needles, or sutures.

One embodiment provides a penile prosthetic having an insertion tool contained inside of an inflatable penile implant. The inflatable penile implant is sized for insertion into a dilated corpora cavernosum of a penis and includes a proximal tip that is insertable into the crus penis and a bladder connected to the proximal tip. The bladder includes a distal tip that is insertable into the glans penis. The insertion tool provides the bladder with a column strength that is sufficient for insertion of the bladder into the dilated corpora cavernosum of the penis. The insertion tool remains and is contained between the proximal tip and the bladder after implantation of the penile implant and closure of the corporotomy.

A column strength that is sufficient for insertion of the penile implant into the dilated corpora cavernosum of the penis is a column strength that is stronger than a column strength of the bladder portion of a penile implant. For example, an inflatable penile implant is provided with a soft and pliable inflatable bladder connected to a proximal tip. While the proximal tip is harder and stronger than the rest of the penile implant (to support the implant against the bony structure of the crus penis), the implant has a column strength associated with the least strong component, which is the bladder. The soft and pliable bladder has a column strength in a range from about 4-12 ounces (about one-quarter to about three-quarters of a pound force). The bladder is designed to be compliant when deflated so that the penis is naturally flaccid when the implant is not erect. A consequence of the pliability is that the column strength of the bladder is insufficient to allow the bladder to be pushed into the dilated corpora cavernosum during implantation. For this reason, the bladder is typically towed into position by a Furlow needle attached to a length of suture. The Furlow needle pierces the glans penis and the suture tows the bladder into the dilated corpora cavernosum.

A column strength that is sufficient for insertion of the penile implant into the dilated corpora cavernosum of the penis is a column strength of about 1 pound force or greater, with a realistic upper limit for the column strength being about 20 pounds force. One useful column strength for the penile implant as provided by the insertion tool is in a range from 1-10 pounds force. While the column strength can be larger than 10 pounds force, a surgeon will generally back off from pushing with more than 10 pounds force and inspect the cavity (corpora cavernosum in the distal direction and the dilated crus in the proximal direction) to determine why resistance is being met.

FIG. 1 is a perspective view of one embodiment of an implantable penile prosthetic 20. The penile prosthetic 20 includes a reservoir 22 sized to contain a volume of liquid, a pump 24 connected to the reservoir 22 and operable to move the liquid out from the reservoir 22 and back into the reservoir 22, and a pair of penile implants 26, where one each of the penile implants 26 is body implantable in a corpora cavernosum of a penis. Each penile implant 26 includes a bladder 28 permanently attached to a proximal tip 30. The bladder 28 is inflatable with the liquid from the reservoir 22 and includes a closed distal tip 32 that is insertable into the glans penis, and the proximal tip 30 is insertable into the crus penis and includes a tubing port 34 communicating between the bladder 28 and the pump 24. An insertion tool 40 is contained inside each penile implant 26 between the proximal tip 30 and the bladder 28.

The reservoir 22 is attachable intra-operatively to the pump 24 by tubing 42, and the pump 24 is attachable intra-operatively to each penile implant 26 by separate tubing 44.

The components (the reservoir 22, the pump 24, the implants 26, and the tubing 42, 44) of the penile prosthetic 20 are generally provided unassembled in a kit of parts. The components are assembled immediately prior to surgery, or intra-operatively, as determined by the surgeon. For example, each of the tubing lengths 42, 44 have a portion that is attached to the reservoir 22 and a portion that is attached to the implants 26, respectively, and a portion that is secured to the pump 24. The tubing lengths are connected intra-operatively with some form of tubing connector useful with surgical implants. The components of the penile prosthetic 20 are illustrated in an assembled configuration in FIG. 1.

The reservoir 22 is sized for implantation within the human body, for example within the abdomen. The reservoir 22 is sized to retain a volume of liquid useful in inflating the inflatable bladders 28, for example with a volume in a range from 50-350 cc. One useful size of reservoir 22 contains about 200 mL of liquid. The liquid is aqueous based. During some procedures the liquid is water, and during other procedures the liquid is saline, depending upon the preference of the surgeon. Suitable materials for fabricating the reservoir 22 include silicone, polymers such as urethanes, a blend of polymers with urethane, copolymers of urethane, or the like. In one exemplary fabrication process, one of the suitable materials identified above is molded into a container shape appropriate for implantation in the space of Retzius or in the abdomen.

The pump 24 includes a pump bulb 50 connected to a pump housing 52. The pump bulb 50 is pliant and configured to be repeatedly squeezed by the user of the prosthetic 20 to move liquid into and out of the implants 26. The pump housing 52 contains the valving that operates to allow a one-way flow of liquid from the reservoir 22 to the inflatable bladders 28 in response to a squeezing of the pump bulb 50, and a one-way flow of liquid out of the inflatable bladders 28 back to the reservoir 22 in response to a touch of the deflation button 54.

The penile implants 26 are sized to be implanted into the penis. Each of the penile implants 26 includes one inflatable bladder 28 that is sealed or attached to the proximal tip 30. The inflatable bladders 28 are fabricated from material configured to be flexible when deflated to provide the penis with a natural, flaccid state and expand when inflated with liquid to provide the penis with an erect state. Suitable material for fabricating the inflatable bladders 28 includes silicone, polymers such as urethanes, a blend of polymers with urethane, copolymers of urethane, or the like. Suitable penile implants 26 are available from Coloplast Corp., Minneapolis, Minn.

In one embodiment, the proximal tip 30 has a durometer in a range from 40 Shore A to 70 Shore A and the distal tip 32 is softer than the proximal tip 30 and has a durometer in a range from 0 Shore A to 39 Shore A. The proximal tip 30 is formed of a hardened material adapted to brace against the bony crus penis within the pelvis. The soft distal tip 32 is implanted in the glans penis and is both flexible and pliant to provide the user with a natural-feeling penis tip. The penile implant 26 does away with the use of the Keith needle, and thus does away with the hole formed in the distal tip. Prior devices that have a hole in the distal tip to accommodate the suture that pulls the Keith needle are associated with a harder distal tip that might possibly be less natural feeling to the user. The penile implant 26 allows for crafting the desired and improved shape of the distal tip 32 and is characterized by an absence of a suture tow hole and is noticeably softer than the distal tip of prior devices.

Figure 2:
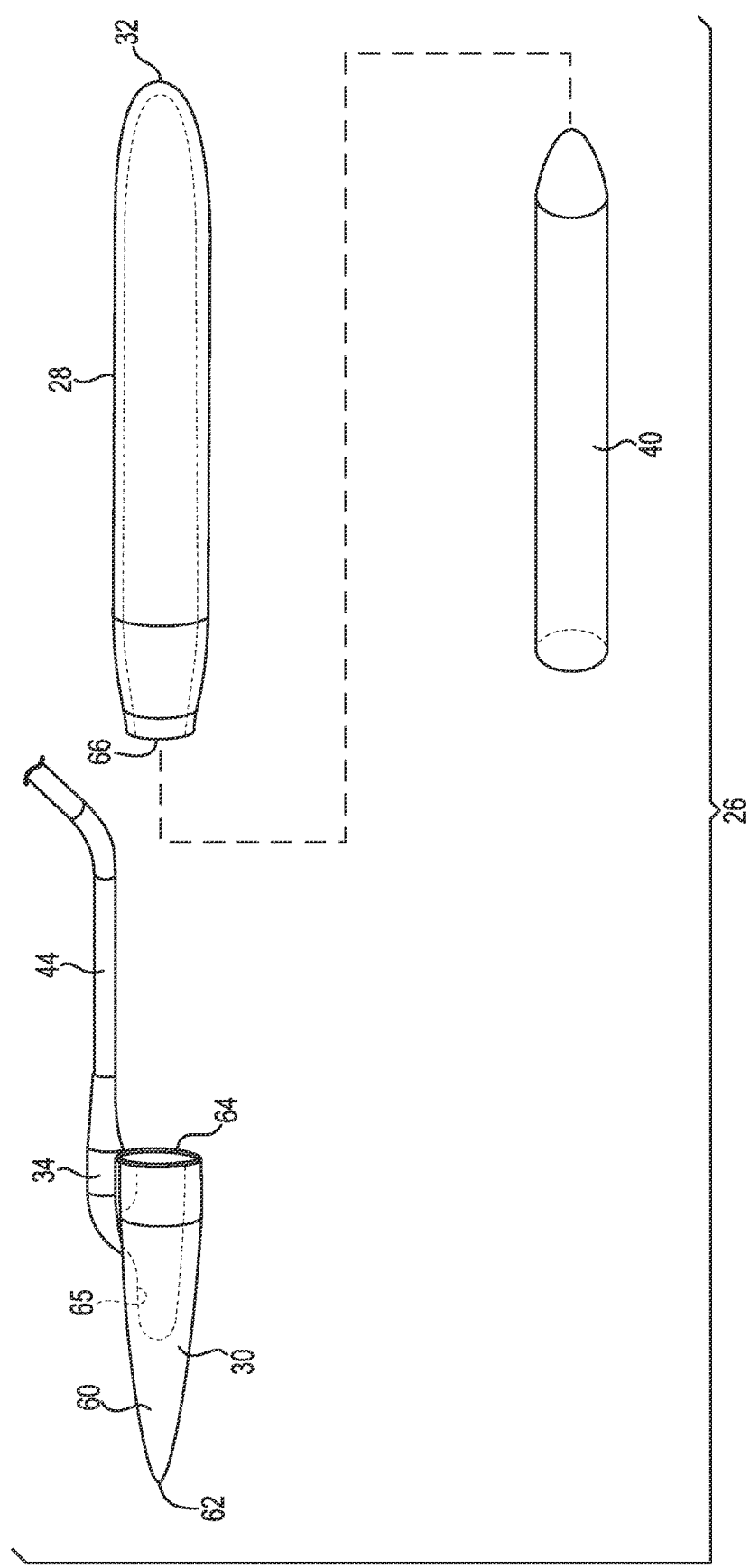
FIG. 2 is an exploded side view of one of the penile implants illustrated in FIG. 1 including an insertion tool, with the insertion tool removed out of containment from inside of an inflatable bladder.

FIG. 2 is an exploded side view of one of the penile implants 26. The penile implant 26 is illustrated prior to assembly with the insertion tool 40 removed out from the inflatable bladder 28.

The inflatable bladder 28 is a thin-walled balloon-like sleeve made of a soft polymer. The distal tip 32 is sealed closed. The inflatable bladder 28 is suitably manufactured in a molding process or other process to fabricate a thin and substantially uniform wall thickness that forms an internal cavity. The style of penile implant that is implanted with a Keith needle and a Furlow device has a reinforced/strengthened distal tip that allows the implant to be towed into place by a suture that is inserted through a hole in the distal tip of the implant. Such a reinforced distal tip potentially has an unnaturally hard configuration that can feel cold or potentially "unnatural" when implanted in a penis. In contrast, the inflatable bladder 28 may be fabricated to include a uniform wall thickness such that the distal tip 32 is uniformly thin, more compliant, and possibly more natural feeling than an implant with a reinforced tip.

The proximal tip 30 includes a proximal portion 60 located between an end 62 and a manifold 64. The proximal portion 60 is generally formed of a solid polymer that is selected to have a hardness property characterized by a durometer in a range from 40 Shore A to 70 Shore A. The hardness of the proximal portion 60 allows the proximal tip 30 to provide a strong foundation for the implant 26 when placed against the crus penis.

The tubing 44 communicates with a liquid access channel 65 formed in the proximal tip 30. The liquid access channel 65 communicates with the inflatable bladder 28 when the inflatable bladder 28 is sealed to the proximal tip 30.

Upon assembly, the insertion tool 40 is inserted into an opening 66 of the inflatable bladder 28. The inflatable bladder 28 with the insertion tool 40 contained inside is sealed against the manifold 64 of the proximal tip 30, for example through the use of an adhesive sealant. Other approaches for permanently attaching the inflatable bladder 28 to the proximal tip 30 are also acceptable.

When the penile implant 26 is assembled, injecting an aqueous liquid through the tubing 44 increases the pressure in the inflatable bladder 28 and causes the inflatable bladder 28 to become firm, which is associated with an erection formed by the penile implant 26.

The insertion tool 40 is placed inside of the inflatable bladder 28 to provide the penile implant 26 with an increased column strength. The increased column strength is useful to allow the surgeon to push the assembled penile implant 26 into a dilated corpora cavernosum of the penis. It is desirable that the penile implant 26 have a sufficient column strength to allow the surgeon to push the implant 26 into the penis during an implantation procedure. However, it is also desirable that the increased column strength associated with the penile implant 26 can be removed or otherwise reduced to allow the implant 26 to occupy a natural, flaccid penis state. Embodiments provide examples of insertion tools that have a sufficient column strength to allow the surgeon to insert the cylinder into a corpora cavernosum during an implantation procedure, where the insertion tool is configured to dissolve or disassociate or lose its column strength within about 60-120 minutes, preferably 30-60 minutes after implantation or exposure to an aqueous liquid. This allows for a stiff insertion tool during insertion and a flaccid insertion tool minutes after implantation.

In one embodiment, the insertion tool 40 is fabricated from a material that dissolves in the presence of an aqueous liquid such as water or saline. One such insertion tool 40 is dissolvable in water having a temperature in a range from 70-100 degrees Fahrenheit.

In one embodiment, the insertion tool 40 is a dehydrated foam. The dehydrated foam is compacted to minimize void spacing in the foam structure in a way that provides the insertion tool 40 with a hardness selected to provide the implant 26 with a column strength suitable for pushing the implant 26 into a dilated corpora cavernosum. Upon contact with an aqueous liquid, the foam tool 40 softens and the column strength reduces to less than 1 pound force.

In one embodiment, the insertion tool 40 includes calcium carbonate. For example, one suitable insertion tool is fabricated as a column of chalk formed of calcium carbonate. The column of chalk has a hardness of a suitably acceptable column strength. In addition, the column of chalk will disassociate or breakdown in the presence of water to form a dispersion of chalk in water. It might be less desirable to have a suspension of the disassociated insertion tool inside of the bladder 28 as this might affect the valves inside of the pump 24 (FIG. 1).

In one embodiment, the insertion tool 40 is fabricated as a cylinder from starch, polysaccharides, derivatives of polysaccharides, sugar, simple sugars, fructose or derivatives of fructose, modified forms of starch, or modified forms of starch and cellulose. Insertion tools fabricated from such materials will dissolve when exposed to water. The insertion tool thus goes into solution and would be imperceptible to the user.

In one embodiment, the insertion tool 40 is fabricated from a compacted fiber material that is associated with an increased column strength for the implant 26 until the compacted fiber is softened by exposure to water. The softened fiber would be contained in the bladder 28 and would be imperceptible, or nearly so, to the user.

In one embodiment, the insertion tool 40 is fabricated from hydrophilic polyurethane to provide a solid shape that is associated with an increased column strength for the implant 26. Upon contact with an aqueous liquid, the hydrophilic polyurethane softens to provide the implant 26 with flaccidity. The softened hydrophilic polyurethane would be contained in the bladder 28 and would be imperceptible, or nearly so, to the user.

In one embodiment, the insertion tool 40 is provided as a resilient, flexible foam material that is coated with a gel. The gel hardens around the foam to provide the implant 26 with an increased column strength until the gel is introduced to water, at which point the gel goes into solution and allows the full material to be soft and flexible. The soft and flexible foam would be contained in the bladder 28 and would be imperceptible, or nearly so, to the user.

In one embodiment, the insertion tool 40 is provided as a malleable penile implant similar to the Genesis® malleable penile implant available from Coloplast Corp., Minneapolis Minn. A malleable form of the insertion tool 40 would provide the user with all the advantages of a malleable penile implant (stiffness and spontaneity), plus the advantages of an inflatable penile implant (girth and natural feeling).

Figure 3A:
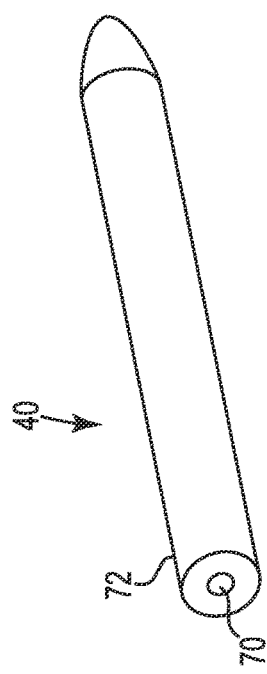
FIG. 3A is a perspective view and FIG. 3B is a cross-sectional view of one embodiment of an insertion tool including a gel coated material
Figure 3B:
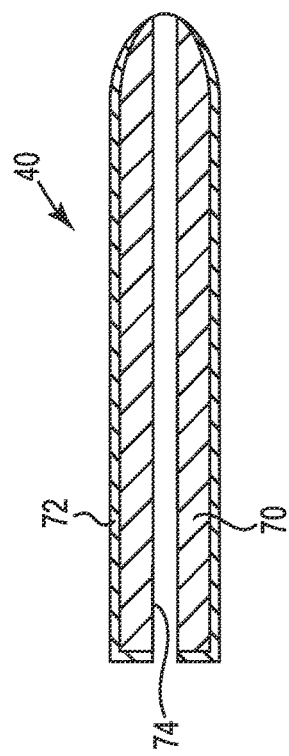
Figure 4:
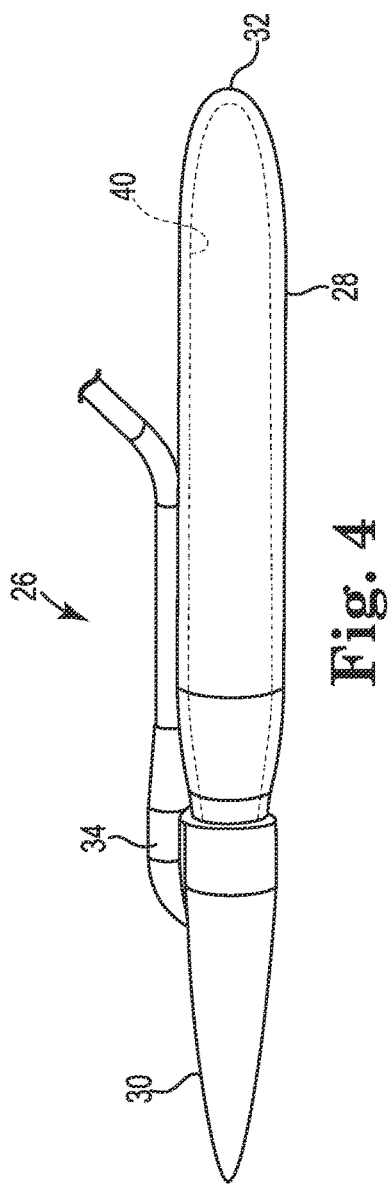
FIG. 4 is a side view of the insertion tool illustrated in FIGS. 3A and 3B contained inside of an inflatable bladder of the penile implant.

FIG. 3A is a perspective view and FIG. 3B is a cross-sectional view of one embodiment of the insertion tool 40, and FIG. 4 is a side view of the insertion tool 40 contained inside of the inflatable bladder 28. The insertion tool 40 includes a core 70 and a gel 72 coated onto the core 70. The core 70 operates to occupy a volume of the inflatable bladder 28. The core 70 is configured to allow the implant 26, when implanted, to have a natural and soft flaccid conformation. The gel 72 is coated onto the core 70 and becomes solid, which provides the insertion tool 40 with a column strength that is suited to allow the implant 26 to be pushed into a dilated corpora cavernosum of the penis. In one embodiment, the gel 72 is coated on an outside surface of the core 70 and an inside surface 72 of the tool is not coated with gel 72. The uncoated inside surface 72 allows an inside surface 74 of the core 70 to absorb water. In this manner, the gel 72 is exposed to aqueous liquid on both its inner surface and its outer surface when the inflatable bladder 28 is inflated with liquid. The gel 72 is configured to dissolve in the aqueous liquid. The gel 72 goes into solution, leaving the soft core 70 inside of the bladder 28 to provide the penis with an acceptable flaccid conformation.

The gel 72 is formulated from an aqueous solution of a gelling agent. Suitable gelling agents include animal protein, collagen, plant polysaccharides or their derivatives like carrageenan, or modified forms of starch and cellulose. The gelling agent can include additives like plasticizers, glycerin, sorbitol, coloring agents, preservatives, or lubricants. The gelling agent is coated onto the core 70 and allowed to harden. The core 70 coated with the hardened gel 72 has an increased column strength over the core 70 alone, and an increased column strength over a penile implant without the insertion tool 40.

Figure 5:
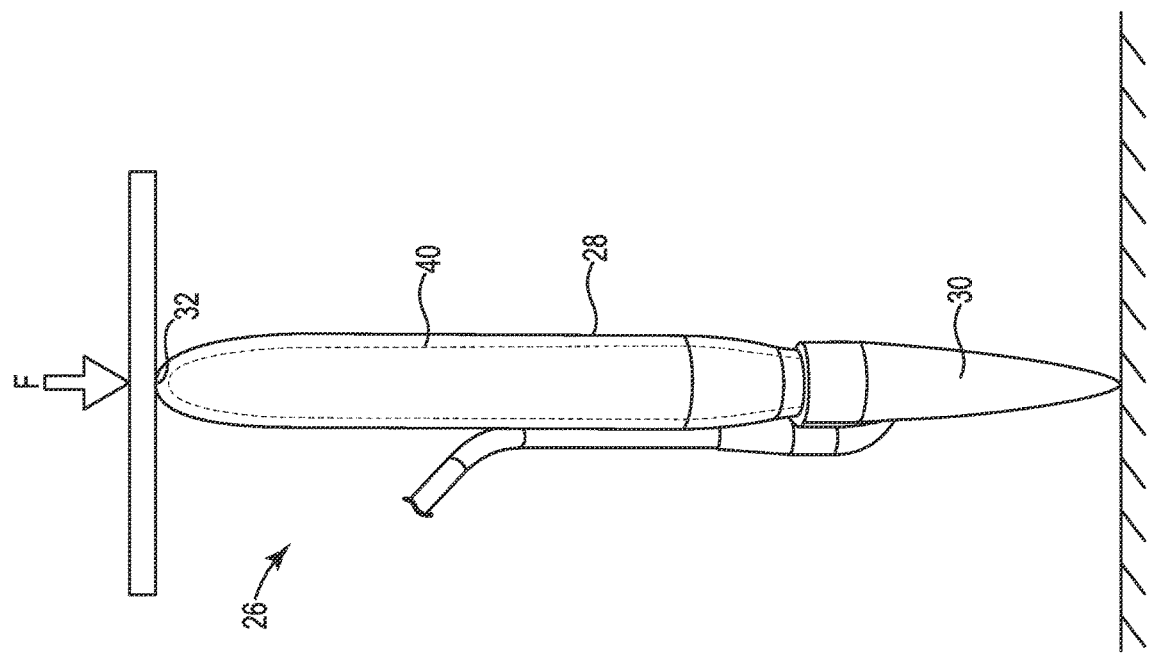
FIG. 5 is a schematic view of one of the penile implants illustrated in FIG. 1 demonstrating the insertion tool providing the penile implant with increased column strength.

FIG. 5 is a schematic view of the insertion tool 40 providing the implant 26 with increased column strength. The implant 26 is inserted between opposing rams of a testing device. A force F is applied to one of the movable rams to apply an axial force to the implant 26. Absent the insertion tool 40, a penile implant will support a column force F of less than 1 pound before buckling under load. With the insertion tool 40, the implant 26 is provided with an effective column strength, which is a column strength above 1 pound force, with a working example of the implant 26 having a range of column strength from 1-20 pounds force. One suitable effective column strength for the implant 26 provided with the insertion tool 40 is an effective column strength in a range from 1.25-10 pounds force.

In one embodiment, the insertion tool 40 has a durometer in a range from 40 Shore A to 70 Shore A prior to exposure to an aqueous liquid.

Figure 6:
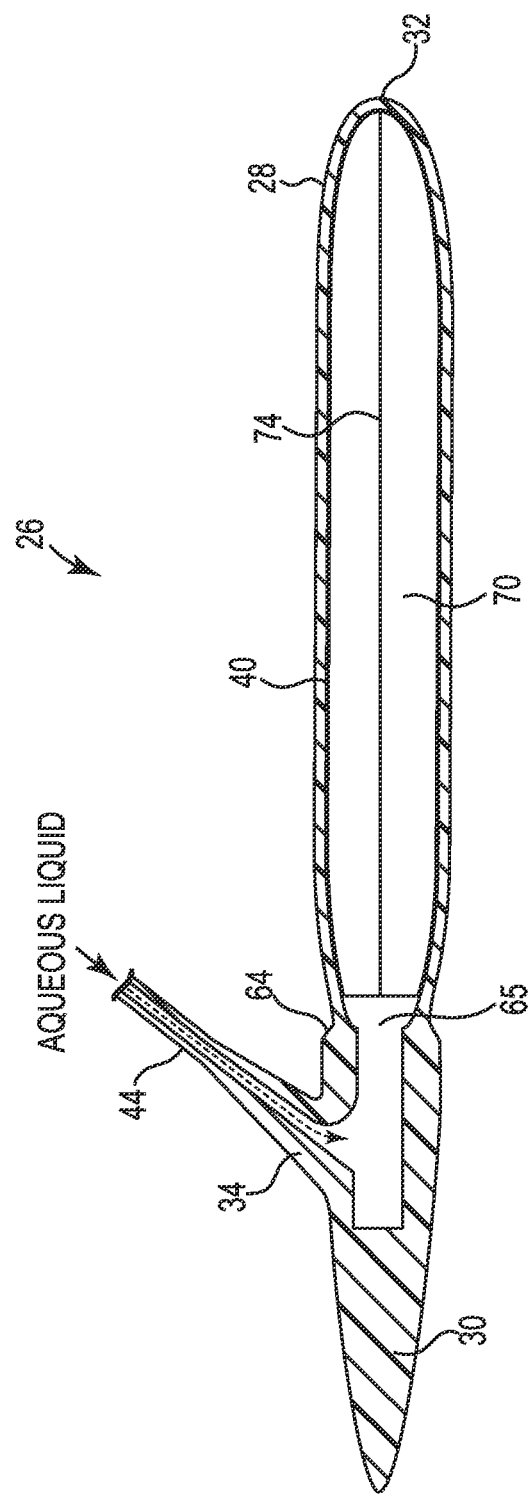
FIG. 6 is a cross-sectional view of the penile implant illustrated in FIG. 4 with the insertion tool in an expanded and softened form.

FIG. 6 is a cross-sectional view of the insertion tool 40 inside of the inflatable bladder 28 and in the presence of an aqueous liquid. When implanted, the reservoir 22 (FIG. 1) provides a source of liquid to the implant 26 through the tubing 44. The aqueous liquid flows through the liquid access channel 65 of the proximal tip 30 and enters the inflatable bladder 28. The liquid comes in contact with the insertion tool 40, which causes the gel 72 (FIG. 3B) coated on the core 70 to go into solution. The core 70 expands and is somewhat constrained by the inflatable bladder 28, such that the inside surface 74 of the annular core is expanded and collapses along a line. The core 70 is soft and resilient and fills the inflatable bladder 28 as the liquid inflates the bladder 28. The core 70 thus provides the implant 26 with a liquid sparing configuration that requires less liquid than a standard implant in order to achieve the same amount of erection/inflation. The tool 40 allows the aqueous liquid to exit the inflatable bladder 28 to allow the implant 26 to assume a flaccid configuration.

Figure 7:
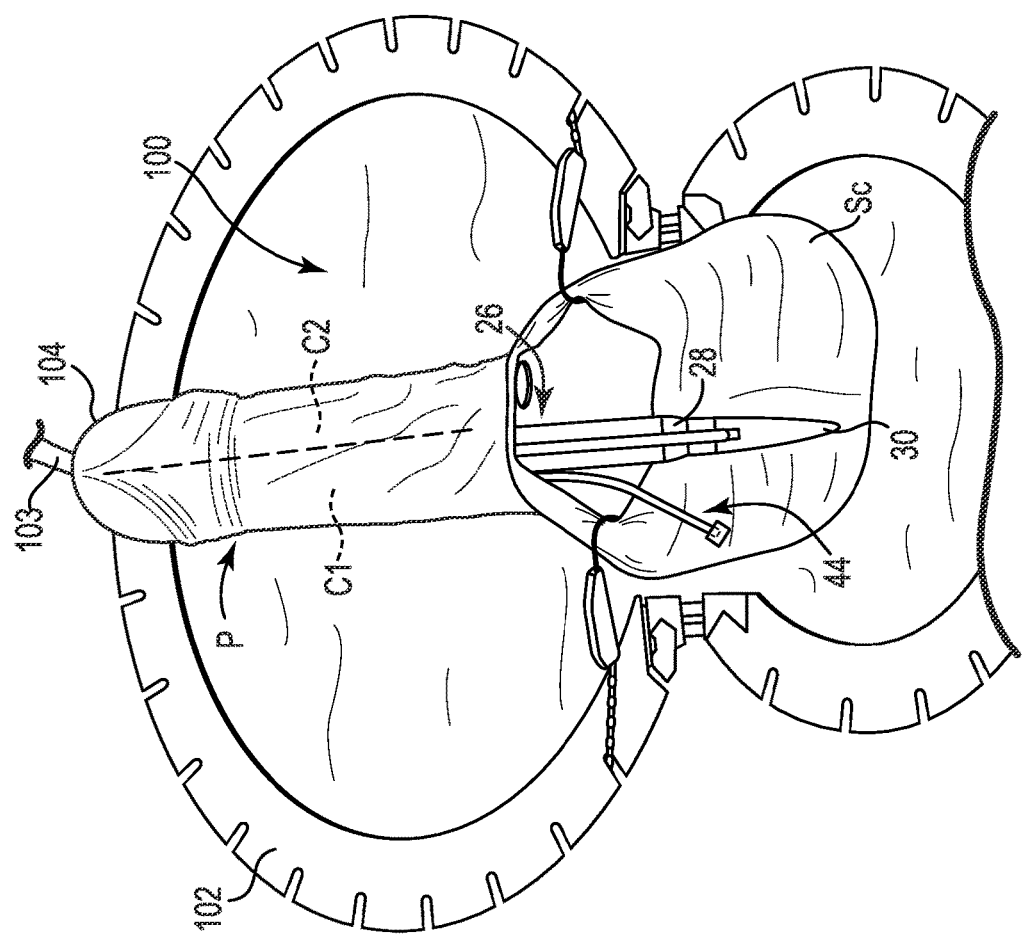
FIGS. 7 and 8 are schematic views of an implantation procedure for placement of the penile implants illustrated in FIG. 1 into a penis.
Figure 8:
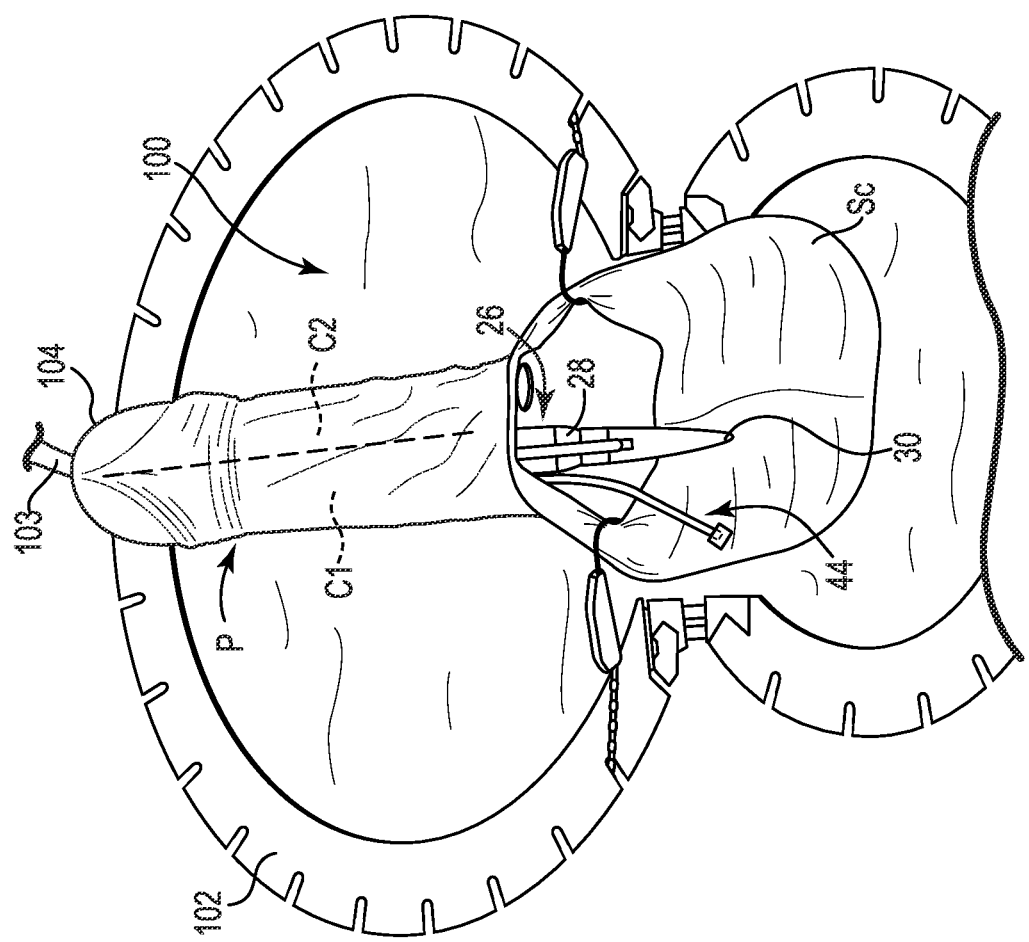

FIG. 7 and FIG. 8 are schematic views of an implantation procedure for the penile implant 26.

The groin area 100 of the patient is shaved, cleaned and suitably prepped with a surgical solution prior to draping with a sterile drape as directed by the healthcare provider's procedures. A retraction device 102, such as those available from Lone Star Medical Products of Stafford, Tex., is placed around the penis P if so desired by the surgeon to establish the surgical field. A catheter 103 is inserted into the urethra U from the distal end 104 of the penis P. The penis P is reclined against the torso and incised to expose the corpora cavernosa (C1 and C2).

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, the surgeon forms a 2-3 cm transverse incision through the subcutaneous tissue of the median raphe of the upper scrotum Sc and dissects down through the Darto's fascia and Buck's fascia to expose the tunicae albuginea of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The surgeon typically will insert a blunt-ended scissors or other elongated tool to separate a portion of the spongiosum material to open a pathway for dilation and measurement of the corpora cavernosum C1, C2. After suitable dilation, the surgeon measures the length of the corpora cavernosa to determine the suitable size for the penile implant 26. In one approach, the surgeon ensures that the appropriately sized penile implant 26 has been selected by measuring the proximal and distal length of each corpora cavernosum C1 and C2. For example, a ruler is inserted into one of the corpora cavernosa C1 or C2 forward in the distal penis toward the glans penis, the distal measurement is recorded by reading the ruler, and the ruler is inserted into the same corpora cavernosa C1 or C2 rearward in the proximal penis toward the crus of the penis to record the proximal length of the corpora by reading the ruler. The distal and proximal measurements would typically be made in reference to a "stay stitch" temporarily placed in the incision. The sum of the distal and the proximal measurements represent the length of that corpora cavernosum, and this information is employed to select a size of the penile implant 26. This procedure is repeated for the other of the corpora cavernosa C1 or C2 to ensure the appropriately sized penile implant 26 has been selected for the companion corpora.

The surgeon holds one of the penile implants 26 between the fingers and the thumb and inserts the penile implant 26 into the corpora cavernosum C1. The insertion tool 40 that is contained within the inflatable bladder 28 provides the penile implant 26 with a column strength that is sufficient to allow the surgeon to push the penile implant 26 in a distal direction to the distal end 104 of the penis. The surgeon would typically infuse the penile implant 26 with a volume of aqueous liquid to ensure that the implant 26 is functioning properly. When infused with saline, for example, the insertion tool 40 softens, dissolves, disassociates, or otherwise becomes flexible losing its column strength after implantation. The surgeon subsequently places the proximal end 30 of the implant 26 into the crus penis.

A similar implantation procedure is performed as the second penile implant 26 is inserted into the second corpora cavernosum C2.

The surgeon connects the tubing between the reservoir 22, the pump 24, and the implants 26 (see FIG. 1) and confirms that the penile prosthetic 20 is operating appropriately. The incision is closed. No Keith needle has been employed and no tow suture was used to place the implant 26 in the penis.

Suitable examples of insertion tools that are contained within the inflatable bladder 28 include tools that dissolve in the presence of water, tools that transition from a solid form to a non-solid form in the presence of water, compacted fibers that relax in the presence of water, solid insertion tools that are inert in the presence of water but are highly malleable, and gel-coated materials that have dual properties of high column strength and softness when exposed to water.

Figure 9A:
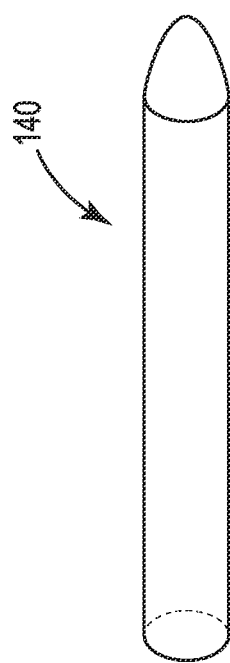
FIG. 9A is a side view of one embodiment of an insertion tool removed from an inflatable bladder of a penile implant.
Figure 9B:
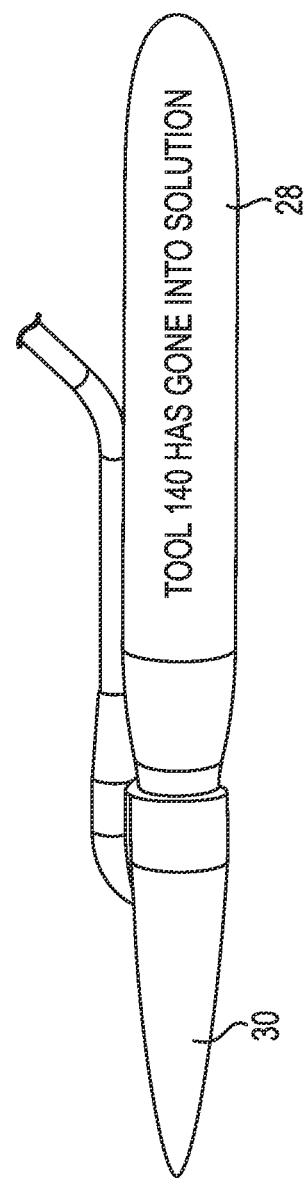
FIG. 9B is a side view of the insertion tool illustrated in FIG. 9A in solution inside of the inflatable bladder of the penile implant.

FIG. 9A is a side view of one embodiment of an insertion tool 140 removed from the inflatable bladder 28 of a penile implant, and FIG. 9B is a side view of the insertion tool 140 after having gone into solution inside of the bladder of the penile implant.

In one embodiment, the insertion tool 140 is fabricated as a solid cylinder formed from starch, polysaccharides, derivatives of polysaccharides, or modified forms of starch and cellulose. The insertion tool 140 has a column strength in a range from 1-12 pounds in the solid form. The insertion tool 140 in its solid form provides the penile implant with a sufficient column strength to allow the surgeon to push the implant into a dilated corpora cavernosum.

In one embodiment, the insertion tool 140 is fabricated as a solid cylinder formed from hydrophilic polyurethane that softens in the presence of an aqueous liquid.

The insertion tool 140 is configured to transition from the solid form with a column strength greater than 1 pound force into a solution with little or no column strength when exposed to aqueous liquid. In one embodiment, the insertion tool 140 is fabricated from a material that dissolves in the presence of water that is at or near the internal human body temperature. While the internal body temperature is generally taken to be 98.6 degrees Fahrenheit, the extremities generally have a temperature of less than 98.6 degrees Fahrenheit. In one example, the insertion tool 140 is dissolvable in water having a temperature in a range from 70-100 degrees Fahrenheit.

FIG. 9B illustrates the insertion tool 140 contained within the inflatable bladder 28 after aqueous liquid has been introduced into the penile implant. The penile implant has been implanted into the dilated corpora cavernosum by the surgeon. The insertion tool 140 has gone into solution, to allow the inflatable bladder 28 to be flaccid when deflated to provide the user with a natural penis sensation.

Figure 10A:
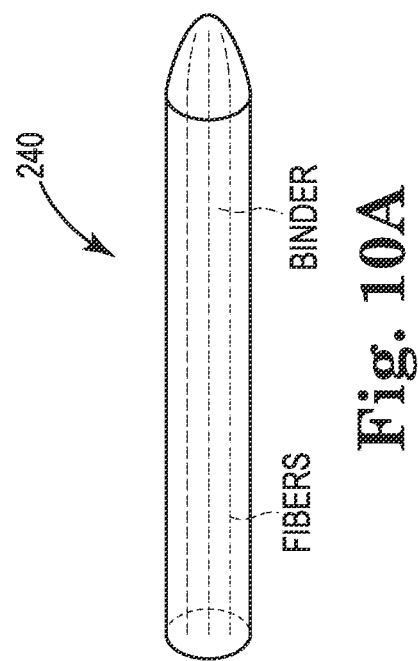
FIG. 10A is a side view of one embodiment of a compacted fibrous insertion tool removed from an inflatable bladder of a penile implant.
Figure 10B:
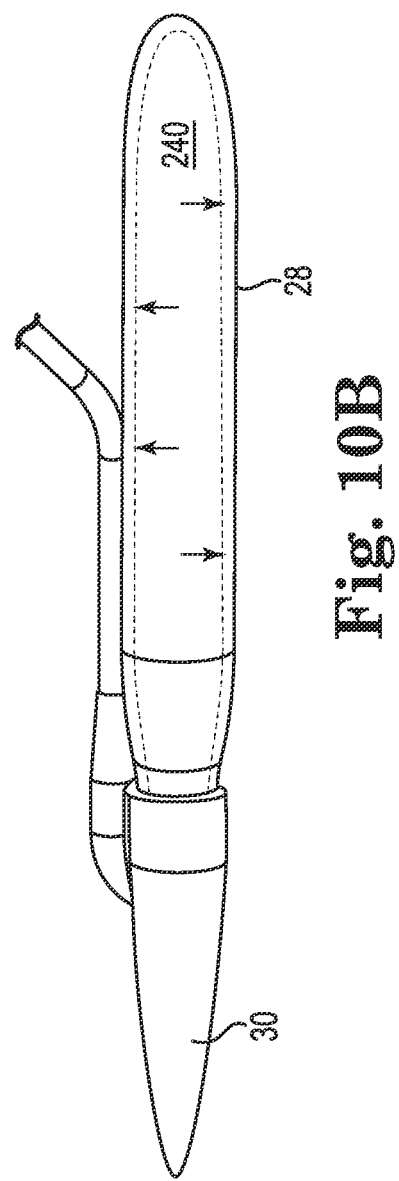
FIG. 10B is a side view of the insertion tool illustrated in FIG. 10A in an expanded fibrous form inside of the inflatable bladder of the penile implant.

FIG. 10A is a side view of one embodiment of a compacted fibrous insertion tool 240 removed from an inflatable bladder of a penile implant, and FIG. 10B is a side view of the insertion tool 240 in an expanded fibrous form inside of the inflatable bladder 28.

The insertion tool 240 is formed from a collection of fibers into a cylindrical shape. For example, a collection of natural or synthetic fibers is compacted in a mold to form a cylindrical shape sized to fit inside of the inflatable bladder 28. Suitable natural fibers include cotton fibers or the like, and suitable synthetic fibers include polyester fibers, polypropylene fibers, or nylon fibers. In one embodiment, in aqueous binder is applied to the fibers to hold and maintain the fibers in a compacted state. In the presence of aqueous liquid, the aqueous binder dissolves to allow the compacted fibers to expand to fill the space of the inflatable bladder 28. When assembled, the insertion tool 240 acts as a fluid sparing insert inside of the implant 26, and thus the size of the reservoir 22 (FIG. 1) may be advantageously reduced.

FIG. 10B illustrates the insertion tool 240 contained within the inflatable bladder 28 after aqueous liquid has been introduced into the penile implant. In the presence of aqueous liquid, the binder dissolves to allow the fibers to expand to fill the internal volume of the inflatable bladder 28. When the penile implant is inflated with aqueous liquid, the fibers of the insertion tool 240 occupy a portion of the volume of the inflatable bladder 28, which allows less volume to be moved from the reservoir 22 (FIG. 1) to achieve full inflation of the penile implant 26. This approach is considered to be a fluid-sparing approach that allows the use of a smaller reservoir that is suitable to be implanted between the skin and the musculature of the abdomen.

FIG. 11 is an exploded side view of one embodiment of a penile implant including an insertion tool 340 provided by a malleable rod that is sized to be contained within the inflatable bladder 28 of a penile implant.

The malleable rod insertion tool 340 includes an elastomeric shaft 342 formed around a wire core 346, with a silver wire coil 344 wrapped around the wire core 346. In one embodiment, the shaft 342 is a silicone elastomer shaft and the wire core 346 is a silver wire core. In one embodiment, a portion of the coil 344 and the core 346 is wrapped in a polymer 348 such as urethane to provide a proximal section of the insertion tool 340 with a higher rigidity than is present in a distal section. Alternatively, a portion of the insertion tool 340 is wrapped in a polymer such as a polyester or a polyethylene terephthalate. In one embodiment, both portions of the coil 344 and the core 346 are over-molded with a silicone rubber to form a body 350 of the insertion tool 340.

The insertion tool 340 provides the implant with the relatively high column strength that is sufficient to allow the implant to be pushed into a dilated corpora cavernosum and aids in maintaining an erection. In addition, the insertion tool 340, when contained within the inflatable bladder 28, has a high degree of flexibility provided by the coil 344 and the core 346, which is useful when the implant is made to be flaccid. The user of the implant manually adjusts the position of the insertion tool 340 between an erect position suited for intercourse, to a non-erect position that simulates a flaccid penis.

Embodiments of the penile prosthetic include an insertion tool that is dissolvable in an aqueous liquid, which advantageously allows the insertion tool to soften or dissolve after having provided the implant with an effective column strength that allows the surgeon to implant the device without a Keith needle or tow suture.

Embodiments of the penile prosthetic include an insertion tool that is dissolvable in an aqueous liquid having a temperature in a range from 70-100 degrees Fahrenheit, which advantageously allows the insertion tool to dissolve after implantation in the human body.

Embodiments of the penile prosthetic include an insertion tool that includes a core and a gel coated on the core, which advantageously allows the gel of the insertion tool to dissolve away (leaving the soft core in the bladder) after having provided the implant with an effective column strength that allows the surgeon to implant the device without a Keith needle or tow suture.

Embodiments of the penile prosthetic include an insertion tool having an elastomeric shaft formed around a wire core, which advantageously provides the implant with the advantages of a stiff but flexible malleable implant and an inflatable implant. A wire core is formed from silver and an elastomeric shaft formed from silicone provides the insertion tool with high malleability and good rigidity.

Embodiments of the penile prosthetic include an insertion tool formed to include a dehydrated foam. The dehydrated foam is stiff when dry, which advantageously provides the implant with an effective column strength that allows the surgeon to implant the device without a Keith needle or tow suture. The dehydrated foam is soft and flexible when wet by an aqueous liquid, which advantageously allows the insertion tool to soften to provide the user with a flaccid penis when the bladder is not inflated.

Embodiments of the penile prosthetic include an insertion tool formed from a solid of calcium carbonate that is configured to disassociate in an aqueous liquid, which advantageously allows the insertion tool to disassociate into a suspension after having provided the implant with an effective column strength (when solid and dry) that allows the surgeon to implant the device without a Keith needle or tow suture.

Embodiments of the penile prosthetic include an insertion tool formed from starch, polysaccharides, derivatives of polysaccharides, sugar, simple sugars, fructose, derivatives of fructose, modified forms of starch, or modified forms of starch and cellulose. Such an insertion tool is rigid and strong when dry to advantageously allow insertion of the implant into the penis, and dissociates or dissolves when exposed to an aqueous liquid.

Embodiments of the penile prosthetic include an insertion tool formed from a hydrophilic polyurethane core or a compacted fiber core adapted to soften in an aqueous liquid, which advantageously allows the insertion tool to soften after having provided the implant with an effective column strength (when solid and dry) that allows the surgeon to implant the device without a Keith needle or tow suture. This provides the implant with good stiffness for insertion and good softness for a flaccid penis.

Embodiments of the penile prosthetic include an insertion tool contained inside of an inflatable bladder of an implant, which advantageously provides the implant with an implantation column strength in a range from 1-10 pounds force to allow implantation without a Keith needle or tow suture.

Embodiments of the penile prosthetic include an insertion tool with a durometer in a range from 40 Shore A to 70 Shore A, which advantageously provides the implant with an implantation column strength in a range from 1-10 pounds force to allow implantation without a Keith needle or tow suture.

Embodiments of the penile prosthetic include an insertion tool contained inside of an inflatable bladder. The tool allows implantation of the implant without a Keith needle. This has the advantage of forming a more nature, soft distal tip that is more natural in feel and with a durometer in a range from 0 Shore A to 39 Shore A.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A penile prosthetic comprising:
a penile implant having an implantation procedure state and an after-implantation state, the penile implant sized for insertion into a dilated corpora cavernosum of a penis, the penile implant includes a proximal tip that is insertable into a crus penis and an inflatable bladder connected to the proximal tip, the inflatable bladder has a first column strength and includes a distal tip that is insertable into a glans penis; and
a liquid-dissolvable insertion tool contained inside of the inflatable bladder when the penile implant is in the implantation procedure state, to provide the bladder with an effective implantation state column strength that is greater than the first column strength; and
wherein, in the presence of liquid when the penile implant is in the after-implantation state, the insertion tool dissolves into solution with the liquid to provide the inflatable bladder with an effective after-implantation column strength that is less than the implantation state column strength;
wherein the insertion tool includes a core and a gel coated on the core.

2. The penile prosthetic of claim 1, wherein the insertion tool is dissolvable in an aqueous liquid.

3. The penile prosthetic of claim 1, wherein the insertion tool is dissolvable in an aqueous liquid having a temperature in a range from 70-100 degrees Fahrenheit.

4. The penile prosthetic of claim 1, wherein the proximal tip includes a tubing connector that communicates with the inflatable bladder and is attachable to a separate section of tubing attached to a pump.

5. The penile prosthetic of claim 1, wherein the first column strength is in a range from ¼-¾ pounds force, and the effective implantation state column strength is in a range from 1-10 pounds force.

6. The penile prosthetic of claim 1, wherein the insertion tool has a durometer in a range from 40 Shore A to 70 Shore A.

7. The penile prosthetic of claim 1, wherein the proximal tip has a durometer in a range from 40 Shore A to 70 Shore A and the distal tip is softer than the proximal tip and has a durometer in a range from 0 Shore A to 39 Shore A.

8. A penile prosthetic comprising:
a reservoir sized to contain a volume of liquid;
a pump connected to the reservoir and operable to move the liquid out from the reservoir and back into the reservoir;
a penile implant having an implantation procedure state and an after-implantation state that is body implantable in a corpora cavernosum of a penis, the penile implant including a bladder fixed to a proximal tip, where the bladder is inflatable with the liquid from the reservoir and includes a closed distal tip that is insertable into the glans penis, and the proximal tip is insertable into the crus penis and includes a tubing port communicating between the bladder and the pump; and a water-dissolvable insertion tool having a first column strength contained between the proximal tip and the bladder when the penile implant is in the implantation procedure state, characterized in that the insertion tool is adapted to dissolve in water to provide a second column strength that is less than the first column strength when the penile implant is in the after-implantation state.

9. The penile prosthetic of claim 8, wherein the insertion tool provides the penile implant with an effective implantation procedure state column strength that allows the bladder to be pushed in a distal direction into the corpora cavernosum of the penis.

10. A penile prosthetic comprising:
a penile implant having an implantation procedure state and an after-implantation state, the penile implant sized for insertion into a dilated corpora cavernosum of a penis, the penile implant includes a proximal tip that is insertable into a crus penis and an inflatable bladder connected to the proximal tip, the inflatable bladder has a first column strength and includes a distal tip that is insertable into a glans penis; and a liquid-dissolvable insertion tool contained inside of the inflatable bladder when the penile implant is in the implantation procedure state, to provide the bladder with an effective implantation state column strength that is greater than the first column strength; and wherein, in the presence of liquid when the penile implant is in the after-implantation state, the insertion tool dissolves into solution with the liquid to provide the inflatable bladder with an effective after-implantation column strength that is less than the implantation state column strength;

wherein the insertion tool is a solid formed from calcium carbonate that is configured to disassociate in an aqueous liquid.

11. A penile prosthetic comprising:
a penile implant sized for insertion into a dilated corpora cavernosum of a penis, the penile implant includes a proximal tip that is insertable into a crus penis and an inflatable bladder connected to the proximal tip, where the inflatable bladder includes a distal tip that is insertable into a glans penis; and an aqueous liquid-dissolvable insertion tool contained inside of the inflatable bladder, where the aqueous liquid-dissolvable insertion tool is adapted to allow the distal tip of the inflatable bladder to be pushed inside of the dilated corpora cavernosum of the penis and inserted into the glans penis; and wherein, in the presence of at least one of water and saline, the insertion tool dissolves into solution inside of the inflatable bladder.

12. A penile prosthetic comprising:
a penile implant adapted for insertion into a dilated corpora cavernosum of a penis, the penile implant including a proximal tip adapted for insertion into a crus penis, an inflatable bladder connected to the proximal tip, and a distal tip adapted for insertion into a glans penis; and an aqueous liquid-dissolvable insertion tool contained inside of the inflatable bladder;

wherein, in the presence of at least one of water and saline, the insertion tool dissolves into solution inside of the inflatable bladder.

13. The penile prosthetic of claim 12, wherein the insertion tool includes a core and a gel coated on the core.

14. The penile prosthetic of claim 12, wherein the insertion tool is a solid formed from calcium carbonate.

15. The penile prosthetic of claim 12, wherein the insertion tool is formed from a group consisting of starch, polysaccharides, derivatives of polysaccharides, sugar, simple sugars, fructose, derivatives of fructose, modified forms of starch, and modified forms of starch and cellulose.

* * * * *